United States Patent
Dierickx et al.

(10) Patent No.: US 11,555,813 B2
(45) Date of Patent: Jan. 17, 2023

(54) APPARATUS AND METHOD FOR MONITORING A CONDITION OF METALWORKING FLUID OF A METALWORKING FLUID CIRCUIT OF A METALWORKING MACHINE

(71) Applicant: BVBA DIERICKX-TOOLS, Rotselaar (BE)

(72) Inventors: Pieter Dierickx, Rotselaar (BE); Dirk Guillaume Gilbert Dierickx, Rotselaar (BE)

(73) Assignee: BVBA DIERICKX-TOOLS, Wezemaal (BE)

( * ) Notice: Subject to any disclaimer, the term of this patent is extended or adjusted under 35 U.S.C. 154(b) by 452 days.

(21) Appl. No.: 16/353,360

(22) Filed: Mar. 14, 2019

(65) Prior Publication Data
US 2020/0292519 A1    Sep. 17, 2020

(51) Int. Cl.
*G01N 33/28* (2006.01)
*C10N 40/20* (2006.01)

(52) U.S. Cl.
CPC ..... *G01N 33/2888* (2013.01); *G01N 33/2894* (2013.01); *C10N 2040/20* (2013.01)

(58) Field of Classification Search
None
See application file for complete search history.

(56) References Cited

U.S. PATENT DOCUMENTS

| | | | | |
|---|---|---|---|---|
| 4,202,193 A * | 5/1980 | Wilson | ............... | G05D 21/02 72/42 |
| 4,315,421 A * | 2/1982 | Wilson | ............... | B21B 45/0251 72/42 |
| 4,767,982 A * | 8/1988 | Florig | ............... | G01R 27/22 324/640 |
| 5,224,051 A * | 6/1993 | Johnson | ............ | G01N 33/2894 700/169 |
| 5,389,546 A * | 2/1995 | Becket | ............... | G01N 33/2894 436/51 |
| 6,860,142 B2 * | 3/2005 | Seevers | ............. | G01N 33/30 73/61.41 |
| 7,275,420 B2 * | 10/2007 | Discenzo | ........... | G01N 33/2888 73/290 R |
| 9,778,242 B2 * | 10/2017 | Gibbons | ............ | C10M 171/007 |

(Continued)

FOREIGN PATENT DOCUMENTS

DE    19911292 A1    11/2000
DE    102007038603 A1    2/2009

(Continued)

OTHER PUBLICATIONS

English Translation of WO-2019150026-A1 (Year: 2019).*

(Continued)

*Primary Examiner* — Alexander A Mercado
(74) *Attorney, Agent, or Firm* — Banner & Witcoff, Ltd.

(57) ABSTRACT

Monitoring apparatus for monitoring a condition of an aqueous metalworking fluid comprised of water and a lubricant, of a metalworking fluid circuit of a metalworking machine, wherein the at least one measurement element of the apparatus is remote from the metalworking fluid circuit. Method for determining a condition of a metalworking fluid, and, when required, to add water and/or lubricant to the metalworking fluid circuit.

18 Claims, 3 Drawing Sheets

(56) References Cited

U.S. PATENT DOCUMENTS

| | | | |
|---|---|---|---|
| 11,137,110 B2* | 10/2021 | Fitch | G01N 33/2888 |
| 2002/0125899 A1* | 9/2002 | Lvovich | G01N 27/026 |
| | | | 324/698 |
| 2004/0075448 A1* | 4/2004 | Lvovich | G01N 33/2888 |
| | | | 324/707 |
| 2004/0159145 A1* | 8/2004 | Seevers | G01N 33/30 |
| | | | 73/61.59 |
| 2007/0202603 A1* | 8/2007 | Counts | G01N 33/2894 |
| | | | 436/43 |
| 2014/0007657 A1* | 1/2014 | Matsubara | G01N 27/221 |
| | | | 73/53.05 |
| 2015/0064741 A1 | 3/2015 | Gibbons et al. | |
| 2018/0313755 A1* | 11/2018 | Hatch | G01N 21/85 |

FOREIGN PATENT DOCUMENTS

| | | | | |
|---|---|---|---|---|
| DE | 102010028319 A1 | 11/2011 | | |
| DE | 102010035228 A1 | 3/2012 | | |
| DE | 102013009370 A1 | 12/2014 | | |
| WO | WO-2018163063 A1 * | 9/2018 | ......... | G01N 33/2888 |
| WO | WO-2019150026 A1 * | 8/2019 | ......... | G01N 33/2823 |
| WO | WO-2020126457 A1 * | 6/2020 | ......... | G01N 33/2894 |

OTHER PUBLICATIONS

English Translation of WO-2020126457-A1 (Year: 2020).*
Dec. 1, 2004. Henry Hopper: "A Dozen Ways to Measure Fluid Level and How They Work:", Sensors Online, XP055373566.

* cited by examiner

APPARATUS AND METHOD FOR MONITORING A CONDITION OF METALWORKING FLUID OF A METALWORKING FLUID CIRCUIT OF A METALWORKING MACHINE

FIELD OF THE INVENTION

The disclosure relates to a metalworking machine, in particular to a metalworking machine having an individual metalworking fluid circuit.

BACKGROUND OF THE INVENTION

Metalworking machines are typically used for automated or semi-automated working of a metallic workpiece, by means of a working tool such as a cutting tool, a milling tool or a machining tool. Such metalworking machines employ a metalworking fluid to lubricate and cool the interface between the working tool and the workpiece. In addition to cooling and lubrication, the metalworking fluid may carry away the shavings and/or chips of material removed from the workpiece.

Often, a water-based metalworking fluid is used comprising a water component, a lubricant fluid component and, preferably, an additive component. The lubricant fluid component may comprise mineral oil, synthetic oil or semi-synthetic oil. In addition, the metalworking fluid may comprise additives, such as corrosion inhibitors, emulsifiers, microbiocides etc. The oil, whether mineral, synthetic or semi-synthetic, is soluble in the water and provides for the lubrication function of the metalworking fluid. The water of the metalworking fluid mainly provides for the cooling function.

A water-based, or aqueous, metalworking fluid is advantageous in use in view of the relative high heat absorption capacity of the fluid, they may be more economical and/or less hazardous than other types of metalworking fluids.

However, a water-base metalworking fluid may be susceptible to evaporation, may provide a medium for the growth of biological contaminants, such as bacteria, mould or other micro-organisms which degenerate the metalworking fluid.

Evaporation, in particular of the water in the water-based fluid, may result in a changed concentration of the fluid between the water-component and the lubricant fluid-component. A changed concentration may deteriorate the cooling and/or lubrication capacity of the metalworking fluid. The concentration of the metalworking fluid may also change due to carrying off of the fluid, in particular of the lubricant or an emulsifier, with the parts or chips removed from the workpiece. Also, during use, the volume of the metalworking fluid present in the metalworking fluid circuit may reduce due to the use, carrying off, evaporation etc.

A huge problem with the water-based metalworking fluid is to prevent and/or to control the growth of microbiological organisms in the fluid. Growth of such microbiological organisms may rapidly decrease the quality of the metalworking fluid, which eventually may result that the metalworking fluid is not suitable for further use. Microbiological organisms in the metalworking fluid grow with increasing rapidity, rapidly deteriorating the quality of the metalworking fluid and making it unusable. Then, the metalworking machine, the metalworking fluid circuit etc. needs to be emptied, cleaned and re-filled with clean metalworking fluid. This is a work-intensive job to do, while, additionally, the machine is in downtime, involving significant costs for cleaning, replacement fluid, downtime etc.

Therefore, it is desirable to monitor the quality of the metalworking fluid, preferably to prevent or timely detect growth of microbiological organisms. Thereto, a number of solutions are proposed in the prior art. For example, it is proposed to measure one or more parameters of the metalworking fluid, such as a refractory index and concentration, or pH and conductivity, or concentration and pH, or the conductivity, or pH and dissolved oxygen. A drawback of the proposed prior art devices may be that the sensors to measure the aforementioned parameters are positioned in the metalworking fluid circuit, which makes them vulnerable to damages, contaminants etc. As such, the sensors are continuously exposed to the metalworking fluid which may negatively impact the lifetime of the sensors. Also, maintenance and/or replacement of the sensor may be difficult and/or costly. Another drawback of the proposed prior art devices may be that the metalworking fluid circuit is a circuit on which multiple metalworking machines are connected. So, multiple metalworking machines are serviced by the same metalworking fluid. The risk on deteriorating of the metalworking fluid, e.g. due to microorganism growth, may be relatively high and/or the costs of replacement of deteriorated fluid by replacement fluid are relatively high as well. Also, it may be difficult to control a condition of the metalworking fluid and/or to adapt the composition of the metalworking fluid dependent on the metalworking process. Also, such devices may be complex and it may not be possible to retrofit existing machines with such devices.

Publication DE 102013009370 describes a device for measuring fluid parameters in a fluid pipe using a pair of condenser measurement electrodes. The pair of condenser measurement electrodes is arranged spirally around a central axis of the fluid pipe such that the distance between the electrodes is constant over the length of the spiral winding. The fluid pipe in which the condenser measurement electrodes are arranged, can be connected in a fluid circuit, such that at one end of the fluid pipe, fluid flows in, and at the other end of the fluid pipe, the fluid flows out. During passage of the fluid in the fluid pipe, along the electrodes, a fluid parameter is measured.

SUMMARY OF THE INVENTION

Embodiments of the present disclosure relate to a device for monitoring the quality of the metalworking fluid that obviates at least one of the above mentioned drawbacks. In particular embodiments, such a device is compact, relatively easy to use and to maintain and, advantageously, may be suitable for retro-fitting on an existing metalworking machine.

Thereto, a first aspect of the disclosure provides for a monitoring apparatus for monitoring a condition of an aqueous metalworking fluid comprised of water and a lubricant, of a metalworking fluid circuit of a metalworking machine, comprising a housing having a sample inlet for receiving a sample of metalworking fluid there through from the metalworking fluid circuit; an outlet for discharging the sample of metalworking fluid to the metalworking fluid circuit after measurement; a water connection for connecting to a water feed line; a lubricant connection for connecting to a lubricant feed line; comprising measurement elements arranged in the housing for measuring pre-determined parameters of the sample of metalworking fluid.

By providing such a monitoring apparatus having a housing in which the measurement elements are arranged and in which a sample of the metalworking fluid can be measured, a compact self-contained device can be obtained in which the measurement elements are remote from the metalworking fluid circuit. The measurement elements being remote from the fluid circuit means that the measurement elements are not mounted into the fluid circuit, as in the prior art devices, and as such, are not permanently exposed to the metalworking fluid. Instead, the measurement elements are only exposed to the metalworking fluid during a sample run, so not continuously, but in a discrete fashion.

Advantageously, the housing is provided with an inlet for receiving a sample of the metalworking fluid. Preferably, the inlet is connectable to the metalworking fluid circuit, such that, when the inlet is opened, a sample of the metalworking fluid can pass through. For example, the housing can be provided with a pump unit that can pump a sample from the metalworking fluid from the metalworking fluid circuit to the apparatus. Further, the housing is provided with a water connection for connecting to a water feed line. As such, after each measurement run, the measurement elements can be rinsed with water for cleaning. Thus contamination of the measurement elements may be obviated, and, contrary to the prior art, the measurement elements may not permanently be exposed to the metalworking fluid. The housing can be provided with a lubricant connection for connecting to a lubricant feed line. As such, when lubricant is to be added to the metalworking fluid circuit, it can be added via the housing of the monitoring apparatus. For example, a sample can be measured first, e.g. until a desired concentration is obtained, prior to be released in the metalworking fluid circuit. So, a self-contained sample apparatus can be obtained that can monitor pre-determined parameters of the sample of the metalworking fluid, and that allows adjusting of the concentration of the metalworking fluid by means of the water connection and/or the lubricant connection.

Advantageously, the apparatus is provided with at least one measurement chamber. At least one measurement element may be present in, or extend into, the measurement chamber. In another embodiment, all measurement elements may be present in, or extend into, the measurement chamber, or for each measurement element a measurement chamber can be provided, or variants thereof may be possible. By providing such measurement chamber, the sample of metalworking fluid can be supplied to the measurement chamber. Then the measurement run can be done, and after the measurement run, the sample of the metalworking fluid can be discharged into the metalworking fluid circuit and the measurement chamber can be emptied. Preferably, after each measurement run, the measurement chamber and the measurement elements are rinsed with water for cleaning. Thus contamination of the measurement elements may be obviated.

So, contrary to the prior art, there is no continuous measuring of the determined parameters, but a measurement run can be done at specified time intervals. For example a measurement run can be done after a certain event has occurred, such as filling of the circuit with metalworking fluid, or a measurement run can be done at predetermined time intervals, e.g. every hour or every two hours. Also, the time interval may vary depending on the measured parameter values. For example, when deterioration of a parameter value may be detected, the time interval may be shortened to more closely follow up on the monitoring of the condition of the metalworking fluid.

In an advantageous embodiment, a mixer is provided in the measurement chamber. The mixer can be provided to mix the sample of metalworking fluid prior to a measurement run, as to undo some effects that may have occurred during the flow of the sample of fluid from the fluid circuit to the measurement chamber. Also, when water and/or lubricant may have to be added to the fluid circuit, the determined amount of water and/or lubricant is preferably entered into the measurement chamber first, can there be mixed or stirred by the mixer prior to be discharged to the metalworking fluid circuit. So, the added metalworking fluid is already mixed when joining the metalworking fluid circuit, providing for a more optimal mixture with the metalworking fluid already present in the circuit.

The housing of the apparatus is provided with a water connection and a lubricant connection for connecting to a water feed line and a lubricant feed line respectively. The water feed line typically can be a feed line connected to a tap water connection point. The lubricant feed line typically is connected to a container or reservoir containing lubricant. Advantageously, the lubricant, comprising oil, is already provided with the required additives for the metalworking fluid.

By providing the water feed line connection and the lubricant feed line connection onto the apparatus, the apparatus can be more self-contained apparatus, which can be advantageous when water and/or lubricant needs to be supplied, the components can then first be mixed in the apparatus prior to be discharged to the metalworking fluid circuit. Also, this may be advantageous, when the apparatus may be provided with a control unit, that, depending on the measured parameter values, may determine an amount of water and/or an amount of lubricant to be filled. Maintaining a predetermined level of fluid in the circuit and/or a predetermined concentration of the fluid in the circuit may thus be more or fully automated.

Advantageously, the measurement elements are configured to provide the values of the parameters that are measured to a control unit. The control unit may be integrated to the apparatus, i.e. may be arranged in the housing of the apparatus. In another embodiment, the control unit may be remotely located from the apparatus, for example the control unit may be provided on a remote server, or on a mobile communications device, etc. Many variants are possible. By providing such a control unit, the process of monitoring the condition of the metalworking fluid may be more automated, and more information may be provided for example to an operator of such a metalworking machine.

Various parameters can be measured. For example, pH, temperature and/or dissolved oxygen may be measured to give an idea of the micro-organisms growth. When the temperature of the fluid is higher, it is known that micro-organisms may grow more rapidly. Also, the growth of micro-organisms consumes oxygen, so the amount of dissolved oxygen is related to a quantity and/or growth of the micro-organisms. The pH value is then related to the growth of the micro-organisms. Other parameters, such s viscosity, density etc. may be measured as well. Also, the level of the fluid in the metalworking fluid circuit is preferably measured, as there is a minimum amount of fluid required for the operation of the metalworking machine. Further, optical characteristics of the fluid such as the refractory index may be measured, and/or the conductivity may be measured which relate to the concentration of the sampled fluid.

Measuring at least some of these parameters, e.g. pH and refractory index, may provide information about the condition of the metalworking fluid.

Advantageously, the control unit may be configured to receive the values of the measured parameters, and further to determine whether the measured parameter values are within predetermined boundaries. For each parameter, there are predetermined boundaries within which the value of the respective parameter preferably lies. These boundaries may be obtained from external sources, e.g. from a manufacturer of the lubrication fluid setting boundaries for concentration etc., or from experience from a machine operator knowing that the pH preferably is between certain boundaries, etc. This information can be inputted and/or set into the control unit. The control unit may provide an output signal when is determined that a value of a measured parameter is outside the pre-set boundary or boundaries of that respective parameter. This output signal can be a warning signal that can be outputted to an operator of the metalworking machine. For example, the apparatus may comprise a user feedback element that is configured to receive an output signal of the control unit, when a measured parameter value is outside of the predetermined boundaries of the respective parameter. The user feedback element may for example be a warning light, emitting a light signal, probably a flashing light signal, to visually warn a user or an operator, or may be a sound emitter for emitting sound waves to audibly warn a user or an operator. The user feedback element may also be a user interface provided e.g. on the housing of the apparatus on which the information about the respective parameter can be displayed. The output signal of the control unit may also be transmitted to a mobile communication device, or to a control room, or to a remotely located computer etc. Many variants are possible. By providing such an output signal, the user or operator of the metalworking machine is warned that at least one of the measured parameters has a value outside of its preset boundaries.

The operator can then judge whether he may need to take some action and/or what action he might take.

Advantageously, the housing is configured to engage with a metalworking machine, such that, when engaged, the sample inlet is connectable to the metalworking fluid circuit. By engaging the housing to the metalworking machine, no complex connection lines or intermediate components are required, and the sample inlet can be directly connected to the metalworking fluid circuit. Advantageously, engagement elements are provided to the housing for engaging with the metalworking machine. The engagement elements may be holes for receiving fastening elements such as bolts or screws there through, or may be pins to connect with holes in the metalworking machine, etc. Many variants are possible. In an embodiment, the metalworking machine may be provided with seats that are arranged for receiving add-on modules such as a pump module.

Advantageously, the housing of the monitoring apparatus is provided with engagement elements that correspond to a receiving seat of the metalworking machine. As such, the apparatus may easily be fitted to the metalworking machine. In a preferred embodiment, the apparatus is an add-on module for a metalworking machine. A used metalworking machine may thus be easily retrofitted with such an add-on module. Alternatively, new-built metalworking machines can be fitted with such an add-on module, if the customer requires so. The new-built metalworking machine can thus be of a modular design, on which add-on modules, such as the apparatus according to the first aspect, or any pump module, can be fitted when required. This provides for a large flexibility of the metalworking machine, both for the customer and the manufacturer.

A second aspect relates to a method for monitoring a condition of the metalworking fluid in a metalworking fluid circuit of a metalworking machine. The method preferably comprises the steps of sampling an amount of metalworking fluid from the metalworking fluid circuit; measuring at least one predetermined parameter of the sample of metalworking fluid and, after measuring, discharging the sample of metalworking fluid back to the metalworking fluid circuit. By sampling an amount of metalworking fluid, a measurement run can be done on the sample, and contrary to the prior art, there is no continuous measuring and no continuous exposure of the measurement elements to the metalworking fluid. Thereby, the lifetime of the measurement element may be increased. A measurement run can be done at predetermined time intervals, or after an event has taken place. Such an event may be the filling of the metalworking circuit with fluid or supplying additional water and/or lubricant fluid. Also, the time interval between subsequent sample runs may dependent on the results of the previous measurement run. So, when the condition of the metalworking fluid is detected to be decreasing, albeit still within the predetermined boundaries, then the time interval between subsequent sample runs may be shortened to more closely monitor the condition of the metalworking fluid.

Advantageously, it is determined whether a measured parameter value is within a predetermined boundary and an output signal may be outputted when at least one measurement of a parameter is outside of a predetermined boundary.

In another embodiment, the refractory index of the metalworking fluid can be measured by means of a refractometer. The refractory index is related to the concentration of the metalworking fluid. Prior to the first measurement of a newly filled or re-filled metalworking fluid circuit, the refractometer is calibrated. A measurement run with only water is performed, and then a measurement run with the metalworking fluid is done. Based on the refractory indexes of these two measurement runs, a refractory index of the fresh metalworking fluid is determined, serving as a calibration point for further measurements.

The volume in the metalworking fluid circuit preferably is measured by a floater in the tank of the circuit. Preferably, the volume is measured continuously and/or intermittently. The volume of the metalworking fluid in the circuit is likely to decrease during use of the metalworking machine due to evaporation, carrying away with chips and shavings etc. and preferably, the volume is regularly measured. Once the volume of the fluid drops below a certain predetermined boundary, a measurement run to measure the refractory index can be performed. Based on the measured refractory index, the concentration of the fluid available in the circuit can be determined. Further, based on the volume and on the concentration of the metalworking fluid, it can be determined what amount of water and/or what amount of lubricant fluid needs to supplied additionally to refill the circuit until the predetermined volume and/or desired concentration are reached. After refilling the circuit with water and/or lubricant fluid, a measurement run can be done to measure the refractory index and to determine whether the concentration has reached the determined concentration level. Based on this information, it can be determined whether the previously determined amount of water and/or amount of lubricant fluid was sufficient to reach the desired concentration. Such a feedback may be taken into account a next time when re-filling of the circuit is required and the amount of water and/or lubricant fluid have to be determined. So, there may be a learning effect to the method and the control unit may be a learning controller using information from previous measurement runs. This may be advantageous in view of efficient use of, in particular, lubricant fluid, as this may be a relatively expensive component.

A third aspect relates to a control unit configured for monitoring a condition of metalworking fluid of a metalworking circuit of a metalworking machine. By providing such a control unit, the monitoring of the condition of the metalworking fluid can be automated, while the control unit can be provided in the apparatus or remote of the apparatus.

A fourth aspect relates to a system comprising the monitoring apparatus and the control unit.

A fifth aspect relates to a method for retro-fitting a metalworking machine having an individual metalworking fluid circuit with the monitoring apparatus.

A sixth aspect relates to a retro-fitted metalworking machine and to a newly built metalworking machine having such an apparatus.

A seventh aspect relates to a computer program product for monitoring a condition of a metalworking fluid and to a mobile communication device comprising a computer program product.

An eighth aspect relates to a kit of a monitoring apparatus and fixating elements.

BRIEF DESCRIPTION OF THE DRAWINGS

These aspects will be further elucidated with reference to figures of exemplary embodiments. Corresponding elements are designated with corresponding reference signs.

FIG. 1a shows a perspective and schematic view on a metalworking machine including a monitoring apparatus according to a first aspect;

FIG. 1b shows an enlargement of the monitoring apparatus of FIG. 1a;

DETAILED DESCRIPTION OF THE INVENTION

Figure 1:
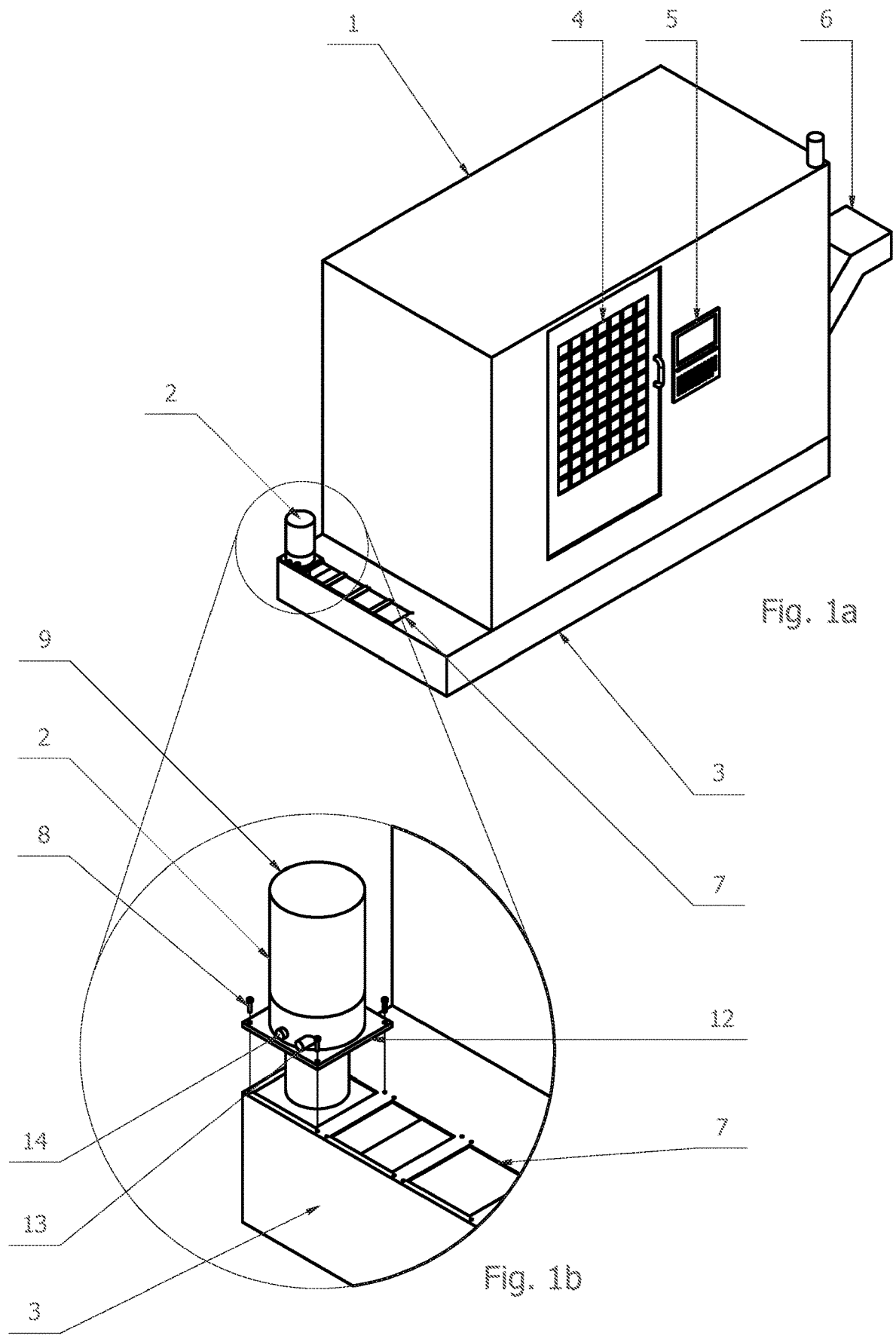

FIG. 1a shows a perspective and schematic view on a metalworking machine 1 including a monitoring apparatus 2 for monitoring a condition of an aqueous metalworking fluid of a metalworking fluid circuit 3 of a metalworking machine 1. A metalworking machine 1 can typically be used for automated or semi-automated working of a metallic workpiece, by means of a working tool such as a cutting tool, a milling tool or a machining tool. Such a working tool can be positioned inside the metalworking machine 1, to which access can be provided via a door 4 to introduce the metal piece to be treated into the machine. The working tool, or the entire metalworking machine 1 can be operated from the outside, for example via an interface 5 on the metalworking machine, or via any other remotely located interface. Such metalworking machines 1 generally employ a metalworking fluid to lubricate and cool the interface between the working tool and the workpiece. In addition to cooling and lubrication, the metalworking fluid may carry away the shavings and/or chips of material removed from the workpiece, for example via an residue outlet 6, draining away a mixture of residual metal shavings and a bit of metalworking fluid. The aqueous metalworking fluid in the metalworking fluid circuit 3 is often a water-based metalworking fluid comprising a water component, a lubricant fluid component and, preferably, an additive component. The lubricant fluid component may comprise mineral oil, synthetic oil or semi-synthetic oil. In addition, the metalworking fluid may comprise additives, such as corrosion inhibitors, emulsifiers, microbiocides etc. The oil, whether mineral, synthetic or semi-synthetic, is soluble in the water and provides for the lubrication function of the metalworking fluid. The water of the metalworking fluid mainly provides for the cooling function. The metalworking machine 1 may be provided with one or more receiving seats 7, in which for example a pump can be installed that is configured to pump around the metalworking fluid in the metal working fluid circuit 3 linked to one or more metalworking tool in the metalworking machine 1.

FIG. 1b shows an enlargement of the monitoring apparatus of FIG. 1a. A monitoring apparatus 2 is provided for monitoring a condition of an aqueous metalworking fluid in a metalworking fluid circuit 3 of a metalworking machine 1. The monitoring apparatus 2 comprises a housing 9 having a sample inlet 10 (see FIG. 2) for receiving a sample of metalworking fluid there through from the metalworking fluid circuit 3 and an outlet 11 for discharging the sample of metalworking fluid to the metalworking fluid circuit 3 after measurement. The inlet 10 and the outlet 11 may also be combined into a single connection between the apparatus 2 and the circuit 3. The inlet 10 and the outlet 11 may comprise an openable and closable valve configured to let a sample of metalworking fluid into the monitoring apparatus 2 only when desired. The housing 9 can be configured to engage with a metalworking machine 1, such that, when engaged, the sample inlet 10 is connectable to the metalworking fluid circuit 3. The housing 9 can be provided with engagement elements 12, for example a transverse protruding sheet and fixation elements, for engagement to the metalworking machine 1. The housing 9, in particular the engagement elements 12, can advantageously be configured to fit to a receiving seat 7 of the metalworking machine 1. When the monitoring apparatus 2 is for example configured as an add-on module for a metalworking machine 1, the housing 9 can advantageously be fixated on the metalworking machine 1, an existing or newly built metalworking machine, in said receiving seats 7 using fixation elements 8, for example screws or bolts or any other suitable fixation means. The monitoring apparatus 2 further comprises a water connection 13 for connecting to a water feed line, and a lubricant connection 14 for connecting to a lubricant feed line. The water feed line can for example be connected to a tap water connection point, e.g. of the mains, or to a water tank, the lubricant feed line can for example be connected to a lubricant container.

Figure 2:
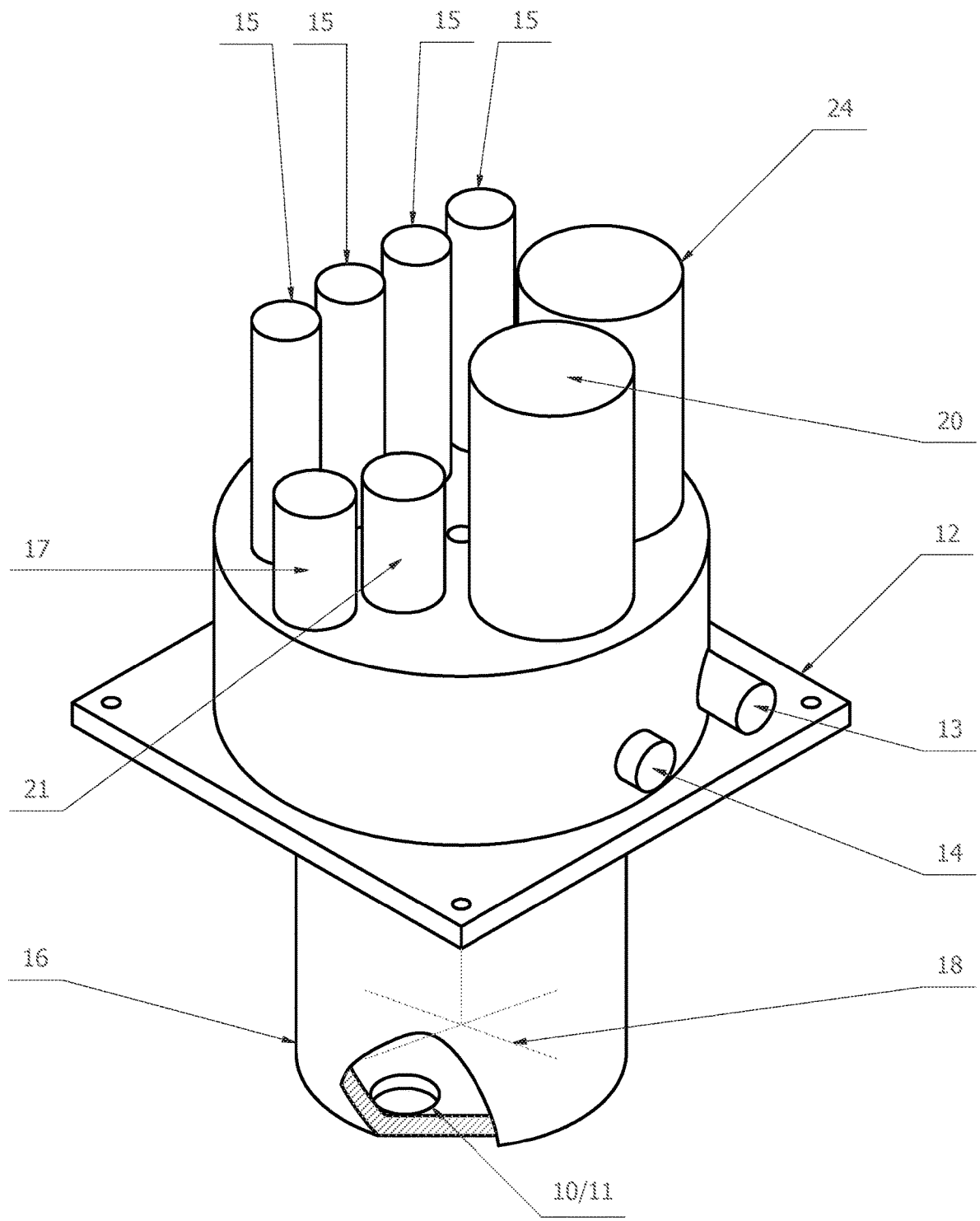
FIG. 2 shows a schematic representation of an inside of the monitoring apparatus of FIG. 1.

FIG. 2 shows a schematic representation of an inside of the monitoring apparatus 2 of FIG. 1. The monitoring apparatus 2 comprises at least one, and preferably a plurality of, measurement elements 15 arranged in the housing 9 for measuring pre-determined parameters of the sample of metalworking fluid. The measurement elements 15 are remote from the metalworking fluid circuit 3, meaning that the measurement elements 15 are not mounted into the fluid circuit 3, as in the prior art devices, and as such, are not permanently exposed to the metalworking fluid. The measurement elements 15 can for example comprise at least one, or preferably more, of a pH-measurement element, a conductivity measurement element, a dissolved oxygen measurement element, a refractometer element, temperature measurement element, and/or a fluid level measurement element, or any other suitable and useful measurement element. The monitoring apparatus 2 can further comprise a measurement chamber 16 into which the at least one measurement element 15 extends. In case of a plurality of measurement elements 15, all measurement elements 15 may be present in, or extend into, the measurement chamber 16. Alternatively, for each measurement element 15, a separate measurement chamber 16 can be provided, or alternatively, a plurality of measurement chambers 16 can be provided, in each measurement chamber one or more measurement elements may extend. A combination of these embodiments is possible as well. The measurement chamber 16 is configured to temporarily receive a sample of metalworking fluid from the metalworking fluid circuit 3, for example via the sample inlet 10 which is connectable to the metalworking fluid circuit 3. By arranging a measurement chamber and at least one measurement element extending in a measurement chamber to measure a sample of metalworking fluid in a housing, a compact device can be provided that is self-contained, meaning that the components needed to perform a measurement run of the sample of fluid are available in the housing. As such, the device can be understood to be modular and may fit onto existing as well as newly-built machines.

After a measurement run, the metalworking fluid can leave the measurement chamber 16 via the outlet 11 for discharging the sample of metalworking fluid to the metalworking fluid circuit 3. A measurement run can be done at predetermined time intervals and/or the time interval between subsequent measurement runs may depend on the condition of the metalworking fluid, as monitored by the monitoring apparatus 2. Also, a measurement run may be performed after an "event", such as the filling of the circuit and/or supplying additional water and/or lubricant to the circuit, has taken place.

Figure 3:
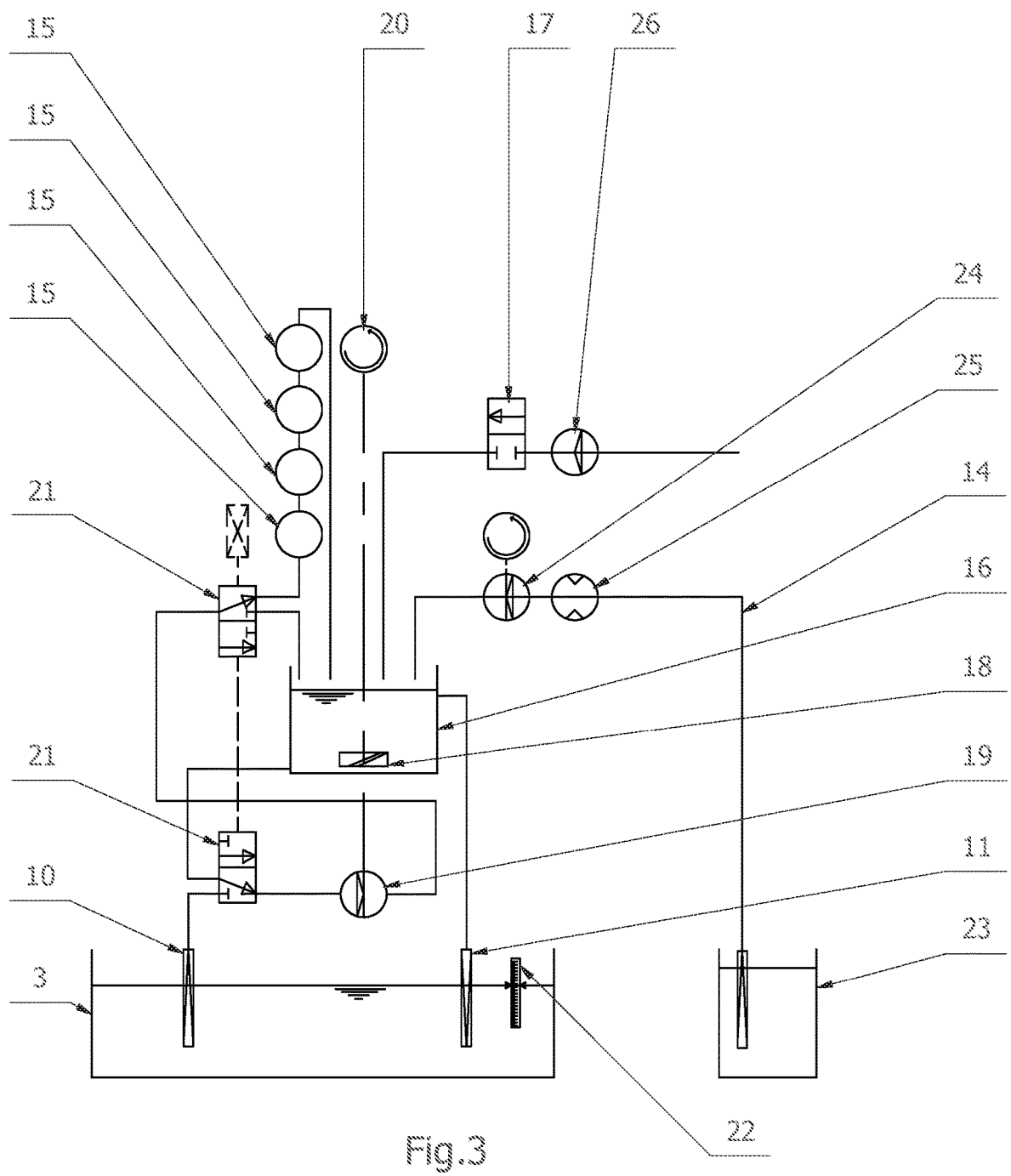
FIG. 3 shows a schematic flow diagram of a method for monitoring a condition of metalworking fluid of a metalworking fluid circuit of a metalworking machine.

Preferably, after each measurement run, the measurement chamber 16 and/or the measurement elements 15 are rinsed with water for cleaning to prevent contamination and continued exposure of these elements 15 to (residues of) the metalworking fluid. Thereto, a clean water valve 17 may be provided within the housing 9. The monitoring apparatus 2 can also be provided with a mixer 18 extending into the measurement chamber 16, to mix a sample of metalworking fluid prior to a measurement run, as to undo some effects that may have occurred during the flow of the sample of fluid from the fluid circuit 3 to the measurement chamber 16. Alternatively, or additionally, when water and/or lubricant may have to be added to the fluid circuit 3, the determined amount of water and/or lubricant can preferably be entered into the measurement chamber 16 first, for example via the water connection 13 connectable to a water feed line, and/or via a lubricant connection 14 which is connectable to a lubricant feed line, to be mixed or stirred by the mixer 18 prior to being discharged to the metalworking fluid circuit 3. So, preferably, the added metalworking fluid is already mixed when joining the metalworking fluid circuit 3, providing for a more optimal mixture with the metalworking fluid already present in the circuit. The monitoring apparatus 2 can further comprise a pump unit 19 (see FIG. 3) arranged in the housing 9 for pumping a sample of the metalworking fluid from the metalworking fluid circuit 3 to the measurement elements 15. The motor 20 of the pump unit 19 can be different from, or the same as, the motor 20 of the mixer 18. Advantageously, the measurement elements 15 are configured to provide the values of the parameters that are measured to a control unit (not shown). The control unit may be integrated to the apparatus 2, i.e. may be arranged in the housing 9 of the apparatus 2. Alternatively, the control unit may be remotely located from the apparatus 2, for example on a remote server, or on a mobile communications device, etc. Many variants are possible. The monitoring apparatus 2 may also include a user feedback element (not shown) that is activated by an output signal of a control unit, when a measured parameter value is outside of a predetermined boundary. The user feedback element can for example comprise a warning light, emitting a light signal, to visually warn a user or an operator, or may be a sound emitter for emitting sound waves to audibly warn a user or an operator. The user feedback element may also be a user interface provided e.g. on the housing of the apparatus on which the information about the respective parameter can be displayed. The output signal of the control unit may also be transmitted to a mobile communication device, or to a control room, or to a remotely located computer etc. The user feedback element may be integrated in an application for a mobile communication device 'app', or a (remote) computer. Many variants known to the person skilled in the art are possible. By providing such an output signal, the operator can be alarmed that one or more parameters have measured values outside of a predetermined boundary FIG. 3 shows a schematic flow diagram of a method for monitoring a condition of metalworking fluid of a metalworking fluid circuit of a metalworking machine. The method includes at least the steps of sampling an amount of metalworking fluid from the metalworking fluid circuit 3, measuring pre-determined parameters on the sample of metalworking fluid, and discharging the sample of metalworking fluid to the metalworking fluid circuit 3. Thereto, the apparatus can comprise a pump unit 19, for example a centrifugal pump driven by a motor 20, for pumping up a sample of the metalworking fluid from the metalworking fluid circuit 3 via the inlet 10. In a preferred embodiment, the apparatus comprises a measurement chamber 16 into which a sample of metalworking fluid can be pumped, and into which the at least one measurement element 15 extends.

Before carrying out a measurement on the sample, the sample can preferably be mixed by the mixer 18 to obtain a better mixture of the sample. Measurement of predetermined values can for example include a pH-measurement, a conductivity measurement, a dissolved oxygen measurement, a temperature measurement, or other measurements. It can for example be determined whether the measured parameter values are within pre-determined boundaries, which can for example be stored in a control unit included in the apparatus or located remotely from the apparatus. When at least one of a measured parameter value is outside the pre-determined boundaries, an output signal can be provided, for example to an operator of the metalworking machine. After finishing the measurements, the sample of metalworking fluid can be released back into the metalworking fluid circuit 3 via the outlet 11. This operation can be done at regular time intervals, or when it is deemed necessary. Measurement elements can preferably be rinsed with water after each sample run. A person skilled in the art will understand that one or more openable and closable valves 21 can be included in the apparatus, for example between the inlet 10 and the measurement chamber 16, and/or between the measurement chamber 16 and the at least one measurement element 15, so that the measurement elements 15 are only exposed to the metalworking fluid during measurements.

In a preferred embodiment, the method can also include an improved way of surveying and filling up the metalworking fluid circuit 3. Instead of observing by eye whether the amount of metalworking fluid is enough or not, the monitoring apparatus is preferably provided with a floater 22 configured to indicate when a level of metalworking fluid in the metalworking fluid circuit 3 descends under a predetermined level. Determining the amount or level of metalworking fluid can for example be done at specified time intervals. Instead of directly filling up the circuit 3 with metalworking fluid as such, it is preferred that the concentration of a sample of the metalworking fluid, for example in the measurement chamber 16, is determined or monitored, for example by measuring the refractory index of a sample of metalworking fluid in the measurement chamber 16, preferably by means of a refractometer. On the basis of the determination of the concentration, for example after having calibrated a refractory index of the metalworking fluid, preferably by means of a refractometer measurement element, it can be determined what amount of water and/or what amount of lubricant fluid needs to be supplied until the concentration and/or the fluid level of the metalworking fluid is within a predetermined boundary. The control unit may then control the supply of the determined amount of water and/or lubricant fluid, for example by controlling water feed line 13 and/or the lubricant feed line 14. Alternatively and/or additionally the amount of water and/or lubricant can for example be transmitted in an output signal to a user feedback element. In order to add the needed amount of water and/or lubricant, the apparatus can comprise a lubricant reservoir 23 connected via the lubricant feed line to the lubricant connection 14. The lubricant feed line can also be provided with a lubricant pump 24 and/or a lubricant flow detection device 25 to detect an amount of lubricant being pumped up by the lubricant pump 24 from the lubricant reservoir 23 to the measurement chamber 16. Analogously, the water feed line may be provided with a water flow detection device 26 to detect an amount of water to be supplied to the measurement chamber 16. Preferably, the valve 17 and/or pump 24 are controlled by the control unit receiving feedback from the detection devices 26 and/or 25. Alternatively, controlling the valves may be done manually by the operator. After supplying the additional amount of water and/or lubricant fluid to the measurement chamber 16, the concentration of the metalworking fluid can be determined again, with or without first mixing the metalworking fluid in the measurement chamber 16. In an alternative, more sophisticated, method, the determination of the amount of water and/or lubricant fluid to be supplied can additionally depend on a feedback of a previous water and/or lubricant supply run. So, a learning control and/or feedback loop can be obtained and the control unit can be a learning controller. When a desired concentration of the metalworking fluid in the measurement chamber 16 has been reached, the metalworking fluid is supplied to the metalworking fluid circuit 3.

The method according to an aspect of the disclosure can be highly automated, for example by adding a control unit (not shown) configured for monitoring a condition of metalworking fluid of a metalworking circuit of a metalworking machine. The control unit may be part of the housing 9 of the monitoring apparatus 2, or may be a separate unit installed remotely from the monitoring apparatus 2. The control unit is configured for receiving values of measured parameters from measurement elements 15 of the monitoring apparatus 2, and can further be configured for determining whether the measured parameter values are within predetermined boundaries. The control unit can also be configured for providing an output signal when at least one of the measured parameter values is outside of a predetermined boundary, preferably to a user feedback element, for example a display, which can also be incorporated into the housing 9 of the monitoring apparatus 2, or which can be placed at a distance from the monitoring apparatus 2. The control unit can further be configured to determine an amount of water and/or an amount of lubricant to be filled when the measured concentration parameter value of the metalworking fluid is outside a predetermined boundary. The control unit can also comprise a computer unit or a mobile communication device, on which a computer program product can be installed for monitoring a condition of a metalworking fluid of a metalworking circuit of a metalworking machine, which computer program product comprises instructions for causing a processor to perform at least one of the steps of the method according to the method as described above.

For the purpose of clarity and a concise description, features are described herein as part of the same or separate embodiments, however, it will be appreciated that the scope of the claims and disclosure may include embodiments having combinations of all or some of the features described. It may be understood that the embodiments shown have the same or similar components, apart from where they are described as being different.

In the claims, any reference signs placed between parentheses shall not be construed as limiting the claim. The word 'comprising' does not exclude the presence of other features or steps than those listed in a claim. Furthermore, the words 'a' and 'an' shall not be construed as limited to 'only one', but instead are used to mean 'at least one', and do not exclude a plurality. The mere fact that certain measures are recited in mutually different claims does not indicate that a combination of these measures cannot be used to an advantage. Many variants will be apparent to the person skilled in the art. All variants are understood to be comprised within the scope defined in the following claims.

The invention claimed is:

1. A monitoring apparatus for monitoring a condition of an aqueous metalworking fluid comprising water and a lubricant, of a metalworking fluid circuit of a metalworking machine, said monitoring apparatus comprising a housing, wherein the housing comprises:
   a sample inlet for receiving a sample of the metalworking fluid there through from the metalworking fluid circuit;
   an outlet for discharging the sample of the metalworking fluid after measurement to the metalworking fluid circuit;
   a water connection for connecting to a water feed line, said water connection being separate from the sample inlet;
   a lubricant connection for connecting to a lubricant feed line, separate from the sample inlet and the water connection;
   wherein at least one measurement element is arranged in the housing and extends into a measurement chamber, for measuring pre-determined parameters of the sample of the metalworking fluid, said measurement chamber containing a motorized mixer,
   wherein said measurement chamber is configured for mixing, using said mixer, fluids received into said measurement chamber from said sample inlet, said water connection, and said lubricant connection, and
   wherein the sample inlet and the outlet are arranged on one side of the mixer, and the water connection, the lubricant connection, and the at least one measurement element are arranged on an opposite side of the mixer, such that the mixer is configured to mix fluid flowing through the measurement chamber both (i) from the sample inlet to the at least measurement element, and (ii) from the water connection and/or lubricant connection to the outlet.

2. The apparatus of claim 1, further comprising a pump unit arranged in the housing for pumping the sample of the metalworking fluid from the metalworking fluid circuit to the at least one measurement element.

3. The apparatus of claim 1, wherein the at least one measurement element is configured for providing the predetermined parameters to a control unit.

4. The apparatus of claim 1, wherein the at least one measurement element is a pH-measurement element, a conductivity measurement element, a dissolved oxygen measurement element, a refractometer element, a temperature measurement element, or a fluid level measurement element.

5. The apparatus of claim 1, further comprising a user feedback element that is activated by an output signal of a control unit when at least one of said predetermined parameters is outside of a predetermined boundary.

6. The apparatus of claim 1, wherein the housing is configured to engage with the metalworking machine, such that, when engaged, the sample inlet is connectable to the metalworking fluid circuit.

7. The apparatus of claim 6, wherein the housing is configured for engagement to the metalworking machine.

8. The apparatus of claim 1, wherein the housing is configured to fit to a receiving seat of the metalworking machine.

9. The apparatus of claim 1, wherein the apparatus is connectable to the metalworking machine.

10. A control unit configured for monitoring the condition of the aqueous metalworking fluid of the metalworking circuit of the metalworking machine, wherein the control unit is configured for receiving values of measured parameters from the at least one measurement element of the apparatus of claim 1, wherein the control unit is further configured for determining whether the measured parameter values are within predetermined boundaries.

11. The control unit of claim 10, wherein the control unit is configured for providing an output signal when at least one of the measured parameter values is outside of a predetermined boundary.

12. The control unit of claim 10, further configured to determine an amount of water and/or an amount of lubricant to be filled when a measured concentration parameter value of the metalworking fluid is outside a predetermined boundary.

13. A system comprising the apparatus of claim 1 and a control unit, wherein the control unit is arranged in the housing of the apparatus.

14. A system comprising the apparatus of claim 1 and a control unit, wherein the control unit is arranged remotely with respect to the apparatus.

15. A method for retro-fitting, the method comprising:
 providing the apparatus of claim 1;
 mounting the apparatus to the metalworking machine, such that the sample inlet is connected to the metalworking fluid circuit;
 connecting the apparatus to the water feed line and the lubricant feed line.

16. A metalworking machine, comprising the apparatus of claim 1 mounted on the metalworking fluid circuit, such that the sample inlet is connected to the metalworking fluid circuit.

17. A metalworking machine comprising the apparatus of claim 1 mounted onto at least one seat of the metalworking fluid circuit.

18. A kit comprising the apparatus of claim 1 and screws or bolts for fixating the apparatus to the metalworking machine.

* * * * *